(12) United States Patent
Santa Maria et al.

(10) Patent No.: US 11,235,027 B2
(45) Date of Patent: Feb. 1, 2022

(54) MODULATION OF HEPARIN-BINDING EPIDERMAL GROWTH FACTOR ACTIVITY FOR TYMPANIC MEMBRANE HEALING

(71) Applicant: The Board of Trustees of the Leland Stanford Junior University, Stanford, CA (US)

(72) Inventors: Peter Luke Santa Maria, Redwood City, CA (US); Yunzhi Peter Yang, Redwood City, CA (US); Sungwoo Kim, Palo Alto, CA (US); Chloe Domville-Lewis, Nedlands (AU)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/981,642

(22) Filed: May 16, 2018

(65) Prior Publication Data

US 2018/0256684 A1    Sep. 13, 2018

Related U.S. Application Data

(63) Continuation of application No. 14/888,936, filed as application No. PCT/US2014/033536 on Apr. 9, 2014, now abandoned.

(60) Provisional application No. 61/823,749, filed on May 15, 2013.

(51) Int. Cl.

| A61K 38/18 | (2006.01) |
|---|---|
| A61K 47/36 | (2006.01) |
| A61L 26/00 | (2006.01) |
| A61K 9/00 | (2006.01) |
| A61K 9/06 | (2006.01) |
| A61K 9/70 | (2006.01) |
| A61F 11/00 | (2006.01) |
| A61L 27/20 | (2006.01) |
| A61L 27/44 | (2006.01) |
| A61F 2/18 | (2006.01) |

(52) U.S. Cl.
CPC .......... *A61K 38/1808* (2013.01); *A61F 11/00* (2013.01); *A61K 9/0046* (2013.01); *A61K 9/06* (2013.01); *A61K 9/7015* (2013.01); *A61K 47/36* (2013.01); *A61L 26/0023* (2013.01); *A61L 26/0066* (2013.01); *A61L 26/0076* (2013.01); *A61L 27/20* (2013.01); *A61L 27/44* (2013.01); *A61F 11/002* (2013.01); *A61F 2002/183* (2013.01); *A61F 2250/0068* (2013.01)

(58) Field of Classification Search
None
See application file for complete search history.

(56) References Cited

U.S. PATENT DOCUMENTS

| 6,132,759 A | 10/2000 | Schacht et al. |
|---|---|---|
| 6,191,109 B1 | 2/2001 | Besner et al. |
| 7,067,492 B2 | 6/2006 | Ny et al. |
| 9,814,779 B2 | 11/2017 | Kim et al. |
| 2003/0133979 A1 | 7/2003 | Burke et al. |
| 2003/0229113 A1 | 12/2003 | Hashimoto et al. |
| 2004/0101560 A1 | 5/2004 | Sawchuk et al. |
| 2007/0038298 A1 | 2/2007 | Sulner et al. |
| 2009/0148486 A1 | 6/2009 | Lu et al. |
| 2009/0192079 A1 | 7/2009 | Santos et al. |
| 2011/0166060 A1* | 7/2011 | Simons ................ A61K 9/0046 514/2.8 |
| 2012/0282173 A1 | 11/2012 | Kimura |
| 2015/0112244 A1 | 4/2015 | Horn-Ranney et al. |

FOREIGN PATENT DOCUMENTS

| WO | 2009/157558 A1 | 12/2009 |
|---|---|---|
| WO | 2013/006908 A1 | 1/2013 |
| WO | 2014/169045 A1 | 10/2014 |

OTHER PUBLICATIONS

Santa Maria et al., Tissue Engineering, Part A, vol. 21, Nos. 9 and 10, pp. 1483-1494, Mar. 2015.*
Santa Maria et al., Otol Neurotol. Aug. 2015; 36(7): 1279-1283. doi:10.1097/MA0.0000000000000795.*
Santa Maria et al., "Heparin Binding-Epidermal Growth Factor-Like Growth Factor for the Regeneration of Chronic Tympanic Membrane Perforations in Mice", Tissue Engineering, Part A, May 2015, pp. 1483-1494, vol. 21, Nos. 9 and 10, Mary Ann Liebert, Inc., New Rochelle, NY.
Raab et al., "Heparin-binding EGF-like growth factor", Biochimica et Biophysica Acta, Dec. 9, 1997, pp. F179-F199, vol. 1333, Issue 3, Elsevier, New York.
Santa Maria et al., "The role of epidermal growth factor in the healing tympanic membrane following perforation in rats", Journal of Molecular Histology, Dec. 2010, pp. 309-314, vol. 41, Issue 6, Springer, Berlin, Germany.
Shirakata et al., "Heparin-binding EGF-like growth factor accelerates keratinocyte migration and skin wound healing", Journal of Cell Science, Feb. 14, 2005, pp. 2363-2370, vol. 118. No. 11, The Company of Biologists, Cambridge, United Kingdon.
Seonwoo et al., "Regeneration of chronic tympanic membrane perforation using an EGF-releasing chitosan patch", Tissue Engineering, Sep. 2013, pp. 2097-2107, vol. 19, Issue 17-18, Mary Ann Liebert, Inc., New Rochelle, NY.
Johnson et al., "Controlled delivery of heparin-binding EGF-like growth factor yields fast and comprehensive wound healing", J Control Release, Mar. 10, 2013, pp. 124-129, vol. 166, No. 2, Elsevier, New York City, NY.

(Continued)

*Primary Examiner* — Marianne P Allen
(74) *Attorney, Agent, or Firm* — Bret E. Field; Bozicevic, Field & Francis LLP

(57) ABSTRACT

Compositions and methods are provided for the generation or treatment of chronic tympanic membrane perforation by modulation of HB-EGF activity.

18 Claims, 10 Drawing Sheets

(56) References Cited

OTHER PUBLICATIONS

Ma et al. "Topical treatment with growth factors for tympanic membrane perforations: progress towards clinical application," Acta Oto-Laryngol, Sep. 1, 2002, p. 586-599, vol. 122, Issue 6, Informa UK Limited, London, England.

Miyamoto et al. "A novel anti-human HB-EGF monoclonal antibody with multiple antitumor with Multiple Antitumor Mechanisms against ovarian cancer cells," Clin Cancer Res., Oct. 25, 2011, pp. 6733-6767, vol. 17, American Association for Cancer Research, Philadelphia, PA.

Zhang et al.,"Progress in the treatment of tympanic membrane perforation by cell growth factor", Foreign Medical Sciences Section of Otolray Ngology Foreign Medical, 2003, pp. 157-162, vol. 27, No. 3, English Abstract Begins on p. 7.

Santa Maria et al., "Chronic tympanic membrane perforation: a better animal model is needed", Wound Repair and Regeneration, Jul. 23, 2007, 450-458, vol. 15, Issue 4, Wiley, Hoboken, NJ.

Cribbs et al., "Acceleration of partial-thickness bum wound healing with topical application of heparin-binding EGF-ike growth factor (HB-EGF)", J Burn Care Rehabil., Mar. 1, 1998, pp. 95-101, vol. 19, Issue 2, American Burn Association, Chicago, IL.

Kaftan et al., "Delay of tympanic membrane wound healing in rats with topical application of a tyrosine kinase inhibitor", Wound Repair Regen., May 6, 2008, pp. 364-369, vol. 16, Issue 3, Wiley, Hoboken, NJ.

Hakuba et al. (2009) "Basic Fibroblast Growth Factor Combined With Atelocollagen for Closing Chronic Tympanic Membrane Perforations in 87 Patients". Otology & Neurotology 31:118-121.

Santa Maria et al. (2010) "The role of epidermal growth factor in the healing tympanic membrane following perforation in rats", J Mol Hist vol. 41, pp. 309-314.

Acharya, et al. "A pilot study investigating basic fibroblast growth factor for the repair of chronic tympanic membrane perforations in pediatric patients", International Journal of Pediatric Otorhinolaryngology 79 (2015) 332-335.

Chauvin, et al. "Healing large tympanic membrane perforations using hyaluronic acid, basic fibroblast growth factor, and epidermal growth factor", Otolaryngology—Head and Neck Surgery, vol. 121, No. 1, Jul. 1999, pp. 43.

Fina, et al. "Direct application of basic fibroblast growth factor improves tympanic membrane perforation healing", Laryngoscope. Jul. 1993;103(7):804-9.

Fina, et al. "Improved Healing of Tympanic Membrane Perforations with Basic Fibroblast Growth Factor", Journal Growth Factors, vol. 5, 1991, Issue 4, pp. 265-272.

Hakuba, et al. "A New Method for Closing Tympanic Membrane Perforations Using Basic Fibroblast Growth Factor", The Laryngoscope 113(8):1352-5, 2003.

Kanemaru, et al. "Regenerative Treatment for Tympanic Membrane Perforation", Otology & Neurotology, vol. 32, No. 8, 2011, pp. 1218-1223.

Mondain, et al. "Fibroblast Growth Factor Improves the Healing of Experimental Tympanic Membrane Perforations", Acta Oto-Laryngologica, vol. 111, 1991—Issue 2, pp. 337-341.

Mondain, et al. "Histological study of the healing of traumatic tympanic membrane perforation after basic fibroblast growth factor application", Laryngoscope, vol. 103, Issue 3, Mar. 1993, pp. 312-318.

Ramsay, et al. "Effect of epidermal growth factor on tympanic membranes with chronic perforations: a clinical trial", Otolaryngol Head Neck Surg. Oct. 1995;113(4):375-9.

Santa_Maria, et al. "In Response to: Regeneration of Chronic Tympanic Membrane Perforation Using an EGF-Releasing Chitosan Patch", Tissue Engineering: Part A, vol. 19, Nos. 19 and 20, 2013, 2 pages.

Tokumaru, et al. "Ectodomain Shedding of Epidermal Growth Factor Receptor Ligands Is Required for Keratinocyte Migration in Cutaneous Wound Healing", The Journal of Cell Biology, vol. 151, No. 2, Oct. 16, 2000, pp. 209-219.

Xu, et al. "Wound-Induced HB-EGF Ectodomain Shedding and EGFR Activation in Corneal Epithelial Cells", Invest Ophthalmol Vis Sci., Mar. 2004; 45(3): pp. 813-820.

Examination report No. 2 for standard patent application, Australian Application No. 2019200630, dated Mar. 19, 2020, 9 pages.

Aggarwal, et al. "Myringoplasty", J Laryngol Otol. 2006;120:429-32. (Abstract Only).

Astellas, "Astellas Executes License Agreement with Auration Biotech for the Development and Commercialization of AU-935", 2017, https://www.astellas.com/en/news/7796, 1 page.

Ryan, et al. "What is the optimal age to repair tympanic membrane perforations in pediatric patients?", Laryngoscope. 2016;126(10):2201-2.

Santa Maria, et al. "Histology of the Healing Tympanic Membrane Following Perforation in Rats", The Laryngoscope, 2010, The American Laryngological, Rhinological and Otological Society, Inc., pp. 2061-2070.

Santos, et al. "Topical fibroblast growth factor-2 for treatment of chronic tympanic membrane perforations", Laryngoscope Investigative Otolaryngology, 2020, pp. 1-8.

Tokumaru, et al. "Ectodomain shedding of epidermal growth factor receptor ligands is required for keratinocyte migration in cutaneous wound healing", J. Cell Biol. 2000, 151: 209-20.

Fen. et al. "Structural organization and chromosomal assignment of the gene encoding the human heparin-binding epidermal growth factor-like growth factor/diphtheria toxin receptor", Biochemistry, Aug. 10, 1993;32(31):7932-8. Abstract Only.

\* cited by examiner

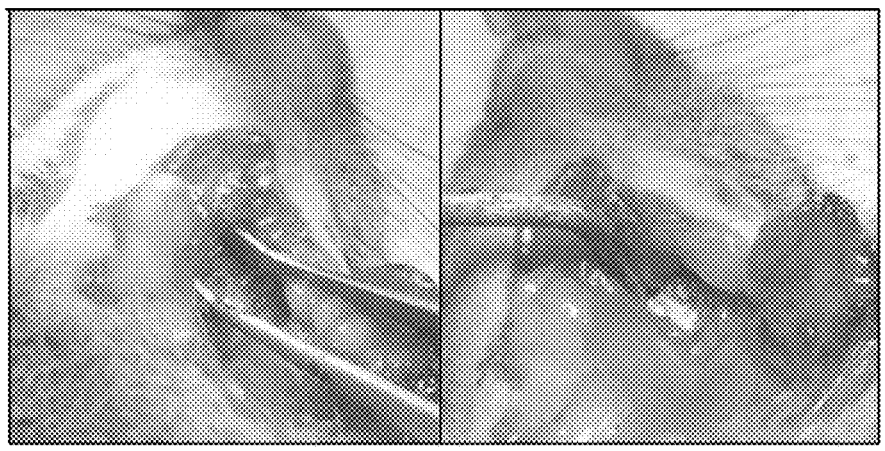

MODULATION OF HEPARIN-BINDING EPIDERMAL GROWTH FACTOR ACTIVITY FOR TYMPANIC MEMBRANE HEALING

CROSS REFERENCE

This application claims benefit and is a Continuation of application Ser. No. 14/888,936 filed Nov. 3, 2015, which is a 371 application and claims the benefit of PCT Application No. PCT/US2014/033536, filed Apr. 9, 2014, which claims benefit of U.S. Provisional Patent Application No. 61/823,749, filed May 15, 2013, which applications are incorporated herein by reference in their entirety.

BACKGROUND OF THE INVENTION

Perforation of the tympanic membrane (TM) most commonly arises as a result of either otitis media or trauma. Clinically, the most common manifestations of TM perforation are conductive hearing loss and chronic infection. The most common cause of TM perforation is infection. Perforations associated with uncomplicated acute otitis media are usually small; the vast majority heal spontaneously once the infection has abated. In addition, large perforations may result from infection with necrotizing organisms. Trauma to the ear is the other major cause of TM perforations. Common causes of injury are blunt and penetrating insults, rapid barometric pressure changes (barotrauma), and excessive acoustic pressure.

Following injury, tissue is known to undergo several stages of healing. Although wound healing in the tympanic membrane involves initial hemostatic and inflammatory stages that are similar to conventional skin healing, the tympanic membrane proliferative and migratory phases are distinctly different from those of other tissues. In most wound healing situations, a granulation tissue bed forms, which serves as a platform upon which re-epithelialization occurs. In healing of the tympanic membrane these events occur in a reverse manner. The squamous epithelial layer initially forms a bridge across the wound, and only then is followed by the re-formation of fibrous component. The TM is unique in that the epidermal layer plays the critical initial role in migration, with the basal proliferating layer controlling this process.

Most tympanic membrane perforations spontaneously heal; however, a number of factors can delay or prevent closure, resulting in a chronic perforation. Persistent perforations commonly arise in the setting of persistent infection that impairs the reparative process. In these situations, the membrane's regenerative healing process is thwarted, preventing chemotaxis and subsequent epithelial migration across the wound. Histologically, in chronic perforations, squamous epithelium grows over the edge of the perforation to meet the medial mucosal layer of the TM.

Treatment for chronic TM perforation include as goals the treatment or prevention of chronic otitis media and restoration of hearing. Conventional therapy includes the use of tissue grafts, e.g. autografts employed in tympanoplasty may use temporalis fascia as an autograft. Superficial temporal fascia composed of fibroblasts in a collagen matrix can be used. Although tympanoplasty with an autologous connective tissue graft is a highly successful method for the repair of persistent TM perforations, it would be beneficial to develop a procedure that does not require microsurgical skills, is less expensive, and could be applied in an office setting. The present invention addresses this need.

PUBLICATIONS

Santa Maria et al. (2010) J Mol Histol. 2010 December; 41(6):309-14. Santa Maria (2011) Thesis, University of Western Australia. Johnson and Wang (2013) J Control Release 166(2):124-9. Ishihara et al. (2003) J Biomed Mater Res A. 64(3):551-9. Tolino et al. (2011) Biochim Biophys Acta. 1810(9):875-8; Shirakata et al. (2005) J Cell Sci. 118(Pt 11):2363-70; Huttenbrink (2005) HNO 53(6):515-6; Ma et al. (2002) Acta Otolaryngol. 122(6):586-99. WO 2007/037514. US 2010/0222265

SUMMARY OF THE INVENTION

Compositions and methods are provided for the treatment of chronic tympanic membrane perforation. In the methods of the invention, a chronically perforated tympanic membrane is topically contacted with an effective dose of heparin binding-epidermal growth factor, HB-EGF, or an agent having HB-EGF activity, for a period of time sufficient to provide for improved healing of the membrane perforation. In some embodiments the dose of HB-EGF is provided in a sustained release formulation; in other embodiments regular administration of a non-sustained release formulation is provided. In some embodiments, a sustained release formulation is biodegradable. In other embodiments sustained release is provided by a device, e.g. a pump or other release device.

The TM being treated is contacted with HB-EGF for a period of time sufficient to improve healing of the TM perforation, i.e. to result in substantial closure of the perforation, e.g. to a perforation of less than about 0.1 $mm^2$ in area. The closure can be monitored visually, including microscopically; functionally, e.g. in reduction of hearing loss; and the like. The period of time for contacting with HB-EGF can be at least one day, at least 3 days, at least 5 days, at least 7 days, at least 10 days, at least 2 weeks, at least 3 weeks; and can be up to one day, up to 3 days, up to 5 days, up to 7 days, up to 10 days, up to 2 weeks, up to 3 weeks, or more according to the needs of the individual.

In certain specific embodiments the effective dose of HB-EGF is provided in a non-ototoxic sustained release formulation, e.g. gel, foam, insert, etc., preferably a biodegradable formulation. In one such embodiment, an effective dose of HB-EGF is formulated in a gel comprising chitosan, poly-lactic acid, and fibrinogen.

In one embodiment, the invention comprises a method of (i) identifying a patient having a chronic perforation of the TM; (ii) contacting the affected TM with an effective dose of HB-EGF, e.g. provided in the form of drops to be administered at suitable intervals, in a device for sustained release of HB-EGF, in a sustained release formulation, etc.; and (iii) monitoring the individual to determine effective closure of the perforation.

Another aspect of the present invention relates to the use of an agent with HB-EGF activity in the manufacture of a medicament for the treatment of a chronic perforation of the TM, wherein the medicament is administered to a patient having a chronic perforation of the TM for a period of time and dose sufficient to effect a closure of the perforation.

Still another aspect of the present invention provides a kit for treatment of chronic perforation of the TM. The kit includes a formulation that provides for an effective dose of HB-EGF, e.g. in the form of drops, devices, formulations, and the like. The kit may also include a delivery device, e.g. ear drop dispenser, syringe for delivery of a formulation, dual barrel syringe for delivering a two part formulation; and the like. The kit may also comprise instructions for use.

In other embodiments, methods are provided for temporary opening of the tympanic membrane, e.g. for insertion of tubes, and the like. In such embodiments a TM is contacted with an effective dose of an HB-EGF inhibitor, including without limitation an inhibitor of EGFR ligand shedding, for a period of time sufficient to create a small perforation in the TM. In some such embodiments a small perforation can be mechanically made prior to contacted with the inhibitor.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 3A-3B. ET before (FIG. 3A) and after (FIG. 3B) occlusion with gutta percha. The procedure in the rat was adapted by opening the bulla using an engraving device with a 0.5 mm burr. Opening the bulla laterally allows the gutta percha to be fed down the ET with less airway retraction. ETs were examined post mortem confirming complete occlusion.

FIG. 7A is a top view showing the ear canal 100 and tympanic membrane 120. The delivery device 127 has a width 132 and length 142. The device comprises a plurality of flanges, 170, arranged lengthwise along the device, which flanges have a length 171 and width 172. FIG. 7B depicts a cross-section of the device.

Figure 1:
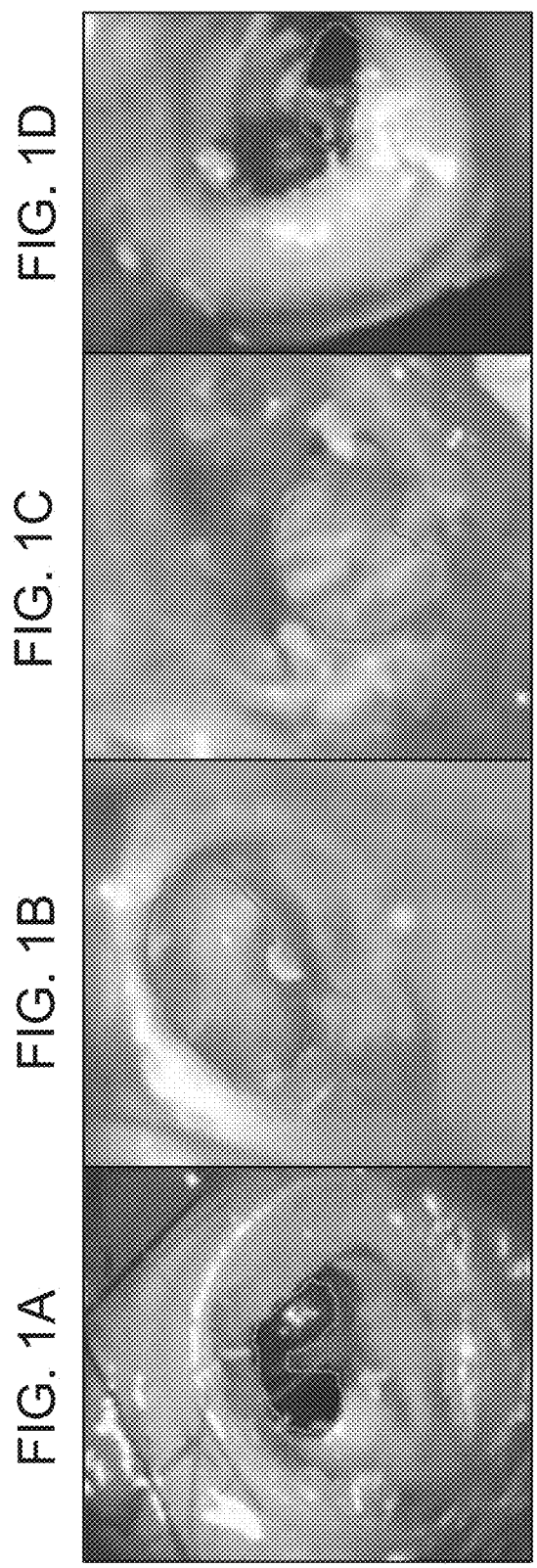
FIG. 1A-1D. Representative images of TMs following perforations treated with OSU8-1 (an inhibitor of EGFR ligand shedding) at (FIG. 1A) day 2 (FIG. 1B) day 14 (FIG. 1C) day 44 (FIG. 1D) day 90 (3 months). The perforation is outlined in blue.

The features and many other advantages of the invention will become better understood by reference to the following detailed description when taken in conjunction with accompanying drawings.

DETAILED DESCRIPTION OF THE EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, illustrative methods, devices and materials are now described.

All publications mentioned herein are incorporated herein by reference for the purpose of describing and disclosing the subject components of the invention that are described in the publications, which components might be used in connection with the presently described invention.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to biological functional equivalency considerations, changes can be made in protein structure without affecting the biological action in kind or amount. All such modifications are intended to be included within the scope of the appended claims.

Definitions

The terms used in this specification generally have their ordinary meanings in the art, within the context of this invention and in the specific context where each term is used. Certain terms are discussed below, or elsewhere in the specification, to provide additional guidance in describing the compositions and methods of the invention and how to make and use them.

Subject. Individuals for treatment with the methods of the invention may be from any mammalian or avian species, including humans. Non-human animals include, without limitation, mammals, laboratory animals such as mice, rats, rabbits, hamsters, guinea pigs, chinchillas etc.; domestic animals such as dogs and cats; and farm animals such as sheep, goats, pigs, horses and cows. A non-human animal of the present invention may be a mammalian or non-mammalian animal; a vertebrate or an invertebrate.

"Treatment" of a subject or "treating" a subject for a disease or condition herein means reducing or alleviating clinical symptoms of the disease or condition such as chronic TM perforation.

"Promote", "enhance", or "improve" tympanic membrane or wound healing generally means increasing the speed by which the wound or perforation heals or reducing the extent of residual scar or keloid or necrotic tissue during or after healing of the wound or perforation.

A "wound" is a break or discontinuity in the structure of an organ or tissue, including epithelium, connective tissue and muscle tissue. Examples of wounds include, but not limited to, skin wounds, bruises, ulcers, bedsores, grazes, tears, cuts, punctures, psoriasis wounds, tympanic membrane perforations, corneal abrasions and disruptions and burns.

"Topical" application refers to non-systemic local administration of an active ingredient to a surface of a wound.

Tympanic membrane. The tympanic membrane is a thin, cone-shaped membrane that separates the external ear from the middle ear in humans and other mammals. Its function is to transmit sound from the air to the ossicles inside the middle ear, and then to the oval window in the fluid-filled cochlea. Hence, it ultimately converts and amplifies vibration in air to vibration in fluid. The malleus bone bridges the gap between the eardrum and the other ossicles.

There are two general regions of the tympanic membrane: the pars flaccida and the pars tensa. The pars flaccida consists of two layers, is relatively fragile, and is associated with eustachian tube dysfunction and cholesteatomas. The larger pars tensa region consists of three layers: skin, fibrous tissue, and mucosa. It is comparatively robust, and is the region most commonly associated with perforations.

Rupture, or perforation of the TM can result from a variety of trauma, from infection, and the like. Perforations of the TM can result in a conductive hearing loss (CHL) that ranges from negligible to 50 dB. Perforations can vary in area and location, e.g. anterior, posterior or both; and in area from about 0.1 to about 60 mm$^2$, generally in the range of about 2.5 to 10 mm$^2$ (see Mehta et al. (2006) Otol Neurotol. 27(2): 136-143). Perforation can be acute or chronic. Acute perforation is generally untreated, as the TM usually heals itself. However, in some individuals the TM does not heal, leading to a chronic perforation.

Chronic perforation of the tympanic membrane. A perforation that does not heal in the absence of treatment, or when treated by conventional methods, e.g. with antibiotic treatment, can be considered a chronic perforation. It will be understood by those of skill in the art that there can be differences in the length of time required for healing between individuals, but generally a perforation that is not healed after up to about 3 months, after up to about 2 months, after up to about 1 month, can be classified as a chronic condition.

Chronic or nonhealing wounds are open wounds that fail to epithelialize and close in a reasonable amount of time. These wounds are clinically stagnant and without evidence of further closure. Chronic wounds may be thought of as lacking appropriate "start" signals. (See, for example, Lorenz and Longaker, in Wounds: Biology, Pathology, and Management, Chapter 7, pp 77-88).

"Heparin binding epidermal growth factor", as used herein, refers to endogenously occurring mammalian, e.g. human, heparin binding epidermal growth factor, allelic heparin binding epidermal growth factor, functional conservative derivatives of heparin binding epidermal growth factor, functionally active heparin binding growth factor fragments and heparin binding epidermal growth factor homologs, such as heparin binding growth factor like growth factor. HB-EGF also relates to variant forms of HB-EGF, e.g. that provide enhanced activity, increased stability, higher yield or better solubility. Compositions for use in the methods of the invention may comprise one or a cocktail of HB-EGF activities, e.g. comprising a plurality of different HB-EGF molecules. Generally an activity of HB=-EGF, as used herein, refers to binding to the cognate receptor, activation of the receptor, biological activities that occur as a result of receptor binding and activation, and the like.

HB-EGF is the predominant growth factor in the epithelialization required for cutaneous wound healing. The mitogenic and migratory effects of HB-EGF on keratinocytes and fibroblasts promotes dermal repair and angiogenesis necessary for wound healing and is a major component of wound fluids. HB-EGF cell surface binding to heparan sulfate proteoglycans enhances mitogen promoting capabilities increasing the rate of skin wound healing, decreasing human skin graft healing times, and promotes rapid healing of ulcers, burns, and epidermal split thickness wounds.

HB-EGF is synthesized as a membrane-anchored mitogenic and chemotactic glycoprotein. HB-EGF is an 87-amino acid glycoprotein that displays highly regulated gene expression. Ectodomain shedding results in the soluble mature form of HB-EGF, which influences the mitogenicity and chemotactic factors for smooth muscle cells and fibroblasts. The transmembrane form of HB-EGF is the unique receptor for diphtheria toxin and functions in juxtacrine signaling in cells. Both forms of HB-EGF participate in normal physiological processes and in pathological processes including tumor progression and metastasis, organ hyperplasia, and atherosclerotic disease. For the purposes of the invention, generally the soluble, mature form of the protein is used. The protein or agent may be substantially pure, e.g. free other proteins, free of cellular material, etc., usually at least about 50% pure, at least about 75% pure, at least about 80% pure, at least about 90% pure, at least about 95% pure, at least about 99% pure.

In a preferred embodiment, a substantially pure preparation of human HB-EGF is used. HB-EGF may be purchased in purified form, or produced by purifying the component from humans or other animals, or by recombinant production in host cells, including prokaryotic host cells such as *S. cerevisiae* or *E. coli*, and, more preferably, mammalian host cells such as CHO cells. The HB-EGF may be wild-type human, a mammalian homolog, or modified/mutated. In particular, fragments of the component which retain at least a part of the desired activity of the full-length component may be used.

In some embodiments the HB-EGF is human HB-EGF, and comprises the amino acid sequence of GenBank Accession: L17032.1 GI 348175 or GenBank Accession: L17033.1 GI 34817 or GenBank Accession: L17032.1 GI 348175, including particularly the soluble mature forms of the proteins described therein.

"Function-conservative variants" are proteins in which a given amino acid residue has been changed without altering overall conformation and function of the protein, including, but not limited to, replacement of an amino acid with one having similar properties (such as, for example, acidic, basic, hydrophobic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, more preferably at least 85%, even more preferably at least 90%, and still more preferably 95%, and which has the same or substantially similar properties or functions as the native or parent protein or enzyme to which it is compared.

As used herein, the term HB-EGF can include variants, homologs and orthologs of the provided sequences. A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids to be maintained in variant sequences. Conservative amino acid substitutions that can be used to provide a variant sequence of the invention typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

The amino acid sequence of a naturally occurring protein can be altered in various ways known in the art to generate targeted changes in sequence and so provide variant sequences of the invention. Such variants will typically be functionally-preserved variants, which differ, usually in sequence, from the corresponding native or parent protein but still retain the desired or exhibit enhanced biological activity and/or function. Various methods known in the art can be used to generate targeted changes, e.g. phage display in combination with random and targeted mutations, introduction of scanning mutations, and the like, and provide a variant sequence of the invention. Included are the addition of His or epitope tags to aid in purification, as exemplified herein. Enzymes modified to provide for a specific characteristic of interest may be further modified, for e.g. by mutagenesis, exon shuffling, etc., as known in the art, followed by screening or selection, so as to optimize or restore the activity of the enzyme, e.g. to wild-type levels, and so provide other variant sequences of the invention.

The term "HB-EGF" also includes biologically active fragments. Fragments of interest include fragments of at least about 20 contiguous amino acids, more usually at least about 50 contiguous amino acids, and may comprise 100 or more amino acids, up to the complete protein, and may extend further to comprise additional sequences.

Modifications of interest to the protein that do not alter primary sequence but provide other variant proteins of the invention include chemical derivatization of proteins, including, for example, acylation, e.g. lauryl, stearyl, myrsityl, decyl, etc. groups, PEGylation, esterification, or amidation. Such modifications may be used to increase the resistance of the enzyme toward proteolysis, e.g. by attachment of PEG sidechains or lauryl groups to surface lysines. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of and provided by the present invention are proteins that have been modified using molecular biological techniques and/or chemistry so as to improve their resistance to proteolytic degradation, oxidation, etc., and to optimize solubility properties or to render them more suitable as a therapeutic agent. For example, the backbone of the protein can be cyclized to enhance stability (see Friedler et al. (2000) *J. Biol. Chem.* 275:23783-23789). Analogs of such proteins include those containing residues other than naturally occurring L-amino acids, e.g. D-amino acids or non-naturally occurring synthetic amino acids.

HB-EGF mimetics. HB-EGF agents of interest also include mimetics, e.g. small molecules, proteins, aptamers, and the like, that provide for the biological activity of HB-EGF. Such activities include binding of HB-EGF to EGF receptors and heparin sulfate proteoglycans on the cell surface.

Pro HB-EGF is synthesized as a type I single transmembrane precursor protein that then undergoes extensive proteolytic processing, termed ectodomain shedding (see, for example, Yan et al. J Cell Biol. 2002; 158(2):221-6; Asakura et al. Nat Med. 2002; 8(1):35-40; Izumi et al. Embo J. 1998; 17(24):7260-72; Nakagawa et al. J Biol Chem. 1996; 271 (48):30858-63). This releases the soluble mature form of HB-EGF. The metalloproteinases (including ADAM 9, 10, 12, 17) responsible for ectodomain shedding of pro HB-EGF predominantly regulate the binding of mature HB-EGF and regulate activation of EGFRs (see Cisse et al. J Biol Chem. 2005; 280(49):40624-31; Peschon et al. Science. 1998; 282(5392):1281-4; Sahin and Blobel FEBS Lett. 2007; 581(1):41-4; Sahin et al. J Cell Biol. 2004; 164(5):769-79). HB-EGF then acts via both EGFR dependent and EGFR independent mechanisms. HB-EGF contains an EGF-like domain thought to be required for EGF family members to bond and activate EGFR (Thompson et al. J Biol Chem. 1994; 269(4):2541-9).

EGF family members can induce juxtacrine, autocrine, paracrine or endocrine signaling depending on the cellular environment because they are cleaved from the membrane by metalloproteinases to form the mature soluble growth factor (Singh and Harris, Cell Signal. 2005; 17(10):1183-93). There are four identified members of the EGFR family (HER1, HER2, HER3 and HER4). They are structurally related tyrosine kinases with a single membrane spanning domain and a domain within the cytoplasm (Plowman, et al. Proc Natl Acad Sci USA. 1993; 90(5):1746-50; Taylor et al. Semin Cell Dev Biol. 2014). Members of the EGF family have differing binding activity to the EGFR family. Unlike EGF, HB-EGF binds to both HER1 and HER4, as do betacellulin and neuregulin2. See Higashiyama et al. Science. 1991; 251(4996):936-9; Chang et al. Nature. 1997; 387(6632):509-12; Carraway et al. Nature. 1997; 387 (6632):512-6; Shing et al. Science. 1993; 259(5101):1604-7. HB-EGF also decreases epithelial markers such as keratins 1, 5, 10 and 14 while increasing cell motility genes such as SNA1, ZEB1, COX-2 and MMP1 (see Stoll et al. J Invest Dermatol. 2012; 132 (9):2148-57).

An "effective amount" or a "therapeutically effective amount" of HB-EGF, or an agent that provides for HB-EGF activity is that dose that, when applied over a period of time, enhances the healing of a chronic TM perforation.

The formulation, i.e. liquid drop, sustained release gel, etc. may comprise HB-EGF, or equivalent activity of an agent providing HB-EGF activity, at a concentration of at least about 1 ng/ml, at least about 10 ng/ml, at least about 100 ng/ml, at least about 1 µg/ml, at least about 10 µg/ml, at least about 100 µg/ml, at least about 200 µg/ml at least about 500 µg/ml, at least about 750 µg/ml, at least about 1 mg/ml, at least about 5 mg/ml, at least about 10 mg/ml, at least about 50 mg/ml, at least about 100 mg/ml, and up to about 10 mg/ml, up to about 25 mg/ml, up to about 50 mg/ml, up to about 100 mg/ml, up to about 500 mg/ml. A formulation for sustained release may be provided at a higher initial concentration than a formulation for repeated administration.

The volume of formulation is typically that which is required to provide useful contact with the tympanic membrane, e.g. up to about 5 µl, up to about 10 µl, up to about 25 µl, up to about 35 µl, up to about 50 µl, up to about 75 µl, up to about 100 µl, up to about 250 µl, up to about 375 µl, up to about 500 µl. Alternatively a dropper can be provided in which the dose is one drop, two drops, three drops, where, as is known in the art, a drop is around about 50 µl. volume.

A therapeutically effective amount provides for a clinically significant response in a subject, in that, e.g., tympanic membrane perforation healing is promoted. Alternatively, a therapeutically effective amount is sufficient to improve a clinically significant wound healing condition in the host.

A sustained or extended release formulation or device can be designed to have VA for drug release, i.e. the length of time for release of half of the active agent, that is appropriate for the starting dose and desired local concentration, e.g. a VA of about 24 hours, about 48 hours, about 3 days, about 4 days, about 5 days, about 1 week, about 10 days, about 2 weeks, about 3 weeks, etc.

A formulation other than sustained or extended release, e.g. liquid ear drops, etc., can be administered at intervals appropriate for maintenance of an effective dose, e.g. about every 3 hours, about every 4 hours, about every 6 hours, about every 12 hours, about every 18 hours, about every 24 hours, about every 48 hours, etc.

Alternatively, an effective amount of HB-EGF, or an agent that provides HB-EGF activity, is an amount that results in a faster healing of a perforation or wound relative to the healing in the absence of the agent. An effective amount could also mean an amount or dose sufficient to increase the local and/or systemic levels of HB-EGF, e.g., to about 10 percent, preferably by about 50 percent, and more preferably by about 100 percent of the level found before administration of the active agent or drug.

The period of time for contacting with HB-EGF can be up to one day, up to 2 days, up to 3 days, up to 5 days, up to 7 days, up to 10 days, up to 12 days, up to 2 weeks, up to 3 weeks, or more according to the needs of the individual.

A "control", "control value" or "reference value" in an assay is a value used to detect an alteration in, e.g., the healing of a perforated tympanic membrane or skin wound, or any other assays described herein. For instance, when studying healing of a tympanic membrane perforation, the inhibitory/stimulatory effect of an agent can be evaluated by comparing the healing of a wound or perforation to that of a control. The control or reference may be, e.g., a predetermined reference value, or may be determined experimentally. For example, in such an assay, a control or reference may be the healing of a similar wound or perforation in an animal not exposed to the drug or active agent, or an animal treated with the same drug or active agent which does not have impaired wound healing capability.

"Inhibitor" includes a natural or synthetic composition or substance that prevents the action of HB-EGF, that lowers the level of HB-EGF or its receptor, that blocks intra-cellular signaling when the HB-EGF triggers its cognate receptor; etc. Inhibitors include nucleic acids, e.g. anti-sense, siRNA, ribozymes, etc.; antibodies specific for HB-EGF or its cognate receptor, small molecules inhibitors, etc. In some embodiments the inhibitor is OSU8-1/KB-R7785 (see-Tokomaru et al. (2000) JCB 151:209-219, herein specifically incorporated by reference). Antibodies specific for HB-EGF, and siRNA, shRNA reagents are known in the art and commercially available (for example see Santa Cruz Biotechnology, or Bertram et al. (2009) Mech. Ageing Dev. 130: 657-669.

Alternatively monoclonal antibodies can be generate by conventional methods for preparation of monoclonal antibodies, any technique which provides antibodies produced by continuous cell line cultures can be used. Examples include the hybridoma technique (Kohler & Milstein, *Nature*, 256:495-497 (1975)), the trioma technique, the human B-cell hybridoma technique (Kozbor et al., *Immunology Today* 4:72 (1983)), and the EBV-hybridoma technique to produce human monoclonal antibodies (Cole, et al., *Monoclonal Antibodies and Cancer Therapy*, Alan R. Liss, Inc., pp. 77-96 (1985)). Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

"Structure", when referring to delivery of HB-EGF or inhibitors of HB-EGF include, but not limited to, any scaffold, polymer, construction, fabrication, mounting, support, disc, block, coating, layer, abutment, backing, device, foam. It also includes using the patient's own tissue, debris or graft to act as a delivery method. The structure may either be applied in its formed state or may be applied as a viscous liquid that then forms a solid state or remains in liquid form.

"Vehicle", when referring to delivery of HB-EGF or inhibitors of HB-EGF includes, but not limited to, any polymer, agent, carrier, instrument, operation, medium, apparatus, appliance, contraption, gadget, tool, widget, implement or utensil. The term "vehicle" also refers to any soluble carrier or excipient including, but not limited to saline, buffered saline, dextrose, water, glycerol and combinations thereof. The formulation should suit the mode of administration. Examples of suitable formulations, known in the art, can be found in *Remington's Pharmaceutical Sciences* (latest edition), Mack Publishing Company, and Easton, Pa.

As used herein, "about" or "approximately" shall mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not.

"Statistically significant" difference means a significance is determined at a confidence interval of at least 90%, more preferably at a 95% confidence interval.

In accordance with the present invention there may be employed conventional molecular biology, microbiology, and recombinant DNA techniques within the skill of the art. Such techniques are explained fully in the literature. See, e.g., Sambrook et al (Molecular Cloning-A Laboratory Manual, Cold Spring Harbor Laboratory Press, 1989); Glover (DNA Cloning: A Practical Approach, Volumes I and II, 1985); Hames and Higgins (Nucleic Acid Hybridization, 1985); Hames and Higgins (Transcription And Translation, 1984); Freshney (Animal Cell Culture, 1986); Perbal (A Practical Guide To Molecular Cloning, 1984); and Ausubel et al. (Current Protocols in Molecular Biology, John Wiley & Sons, Inc., 1994).

Pharmaceutical Formulations

Formulations that may be used in delivering HB-EGF, and HB-EGF agent, or HB-EGF inhibitor or other compositions according to the invention include, but are not limited to, injectable dosage forms, infusions, gel, pastes, balms, waxes, lotions, skin creams, and various other formats for topical administration known in the art. The compositions may also be delivered locally in the form of a powder or solution sprayed onto the wound. Alternatively, the compositions of the invention may be present in wound dressings, pads, band-aids, gauze, or other means applied onto a wound, from which they are transferred to the wound area. Such devices also include slow-release devices, continually releasing HB-EGF or HB-EGF inhibitor or other components for a prolonged period of time. With respect to healing of tympanic membranes, administration of the composition using a gel, spray, or drop-wise application via the outer ear canal, is one preferred embodiment. Injectable dosage forms or infusions comprise a solution of HB-EGF or HB-EGF inhibitor in a pharmaceutically acceptable liquid such as, e.g., isotonic saline, sterile water, or aqueous buffer systems. The delivery vehicle may also include any structure passing through the wound. In the case of the tympanic membrane it includes, but not limited to, ventilation tubes or catheters.

Pharmaceutical compositions can include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the active agent. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via topical routes, e.g. on the surface of the TM, intra-tympanic membrane, trans-tympanic membrane, etc.

Suitable formulations include aqueous and non-aqueous, isotonic sterile injection solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A competent clinician will be able to determine an effective amount of a therapeutic agent to administer to a patient to promote healing of a chronic TM perforation. Utilizing $ED_{50}$ animal data, and other information available, a clinician can determine the safe dose for an individual, depending on the route of administration. Compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials. Typically the dosage will be 0.001 to 100 milligrams of agent per kilogram subject body weight.

The formulation, i.e. liquid drop, sustained release gel, etc. may comprise HB-EGF or equivalent activity of an agent providing HB-EGF activity, at a concentration of at least about 1 µg/ml, at least about 10 µg/ml, at least about 100 µg/ml, at least about 200 µg/ml at least about 500 µg/ml, at least about 750 µg/ml, at least about 1 mg/ml, at least about 5 mg/ml, at least about 10 mg/ml, at least about 50 mg/ml, at least about 100 mg/ml, and up to about 10 mg/ml, up to about 25 mg/ml, up to about 50 mg/ml, up to about 100 mg/ml, up to about 500 mg/ml. A formulation for sustained release may be provided at a higher initial concentration than a formulation for repeated administration. The therapeutically active amount may vary according to factors such as the disease state, age, sex, and weight of the individual. Dosage regime may be adjusted to provide the optimum therapeutic response. For example, more than one divided doses may be administered daily or the dose may be proportionally reduced as indicated by the exigencies of the therapeutic situation.

The volume may be provided as from about 1 to 3 drops, or if administered in a solid or semi-solid form may be a prepared composition of set volume, e.g. from up to about 5 µl to up to about 500 µl volume. The device may be formed into any shape or conformation that will facilitate its use in the target area to promote or inhibit healing. The geometry of a solid or semi-solid form is any that is appropriate for delivery to the tympanic membrane, e.g. a sphere, flattened sphere, film, patch, disk of uniform or non-uniform thickness, and the like.

The formulation can be administered to the subject in a series of more than one administration. For therapeutic compositions, regular periodic administration (e.g., every 4 hours, every 6 hours, every 12 hours, every 24 hours, etc.) will sometimes be required, e.g. where the formulation is provided as a liquid for topical administration.

Formulations suitable for topical, transcutaneous, and transdermal administration may be prepared through use of appropriate suspending agents, solubilizers, thickening agents, stabilizers, and preservatives. Topical formulations may be also utilized with a means to provide continuous administration, for example, incorporation into slow-release pellets or controlled-release patches.

The active agent can also be formulated in a biocompatible gel, which gel can be applied topically or implanted (e.g., to provide for sustained release at a treatment site). Suitable gels and methods for formulating a desired compound for delivery using a gel are well known in the art (see, e.g., U.S. Pat. Nos. 5,801,033; 5,827,937; 5,700,848; and MATRIGEL™). An example of this embodiment is the delivery of the HB-EGF or inhibitor of HB-EGF through the ear canal via a biocompatible liquid or device which then solidifies within the ear canal adjacent to the tympanic membrane and delivers the HB-EGF or HB-EGF inhibitor as the vehicle dissolves over time. The vehicle may be placed in the canal, in the tympanic membrane or within the middle ear.

Formulations may be provided in a unit dosage form, where the term "unit dosage form," refers to physically discrete units suitable as unitary dosages for human subjects, each unit containing a predetermined quantity of protease in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

Aspects of the invention include crosslinked copolymer hydrogel compositions comprising an effective dose of absorbed HB-EGF, as described above. Crosslinked copolymer hydrogel compositions of the invention according to certain embodiments include a copolymer of chitosan and a polyester and a hydrolysable crosslinker. In certain embodiments, crosslinked hydrogels further include fibrinogen. In some such embodiments, crosslinked copolymer hydrogels include a copolymer of chitosan and a polyester and a hydrolysable crosslinker, e.g. polylactide. Crosslinked chitosan-polylactide hydrogels may have a ratio of chitosan to polylactide ranging from 1:1 to 10:1, such as 1:1 to 8:1, where in certain instances, crosslinked chitosan-polylactide hydrogels have a ratio of chitosan to polylactide of 8:1. The weight percentage of chitosan in crosslinked copolymer hydrogels of interest may range from 1% to 99% and the weight percentage of the polyester may also range from 1% to 99%. In some embodiments, copolymer hydrogels include one or more ester and amide linkages between the chitosan and the polyester components. Crosslinked copolymer hydrogels of interest also include a crosslinker. In some embodiments, the crosslinker is configured to hydrolyze under physiological conditions. In some embodiments, the crosslinker may be an acrylate crosslinker, such as a methacrylate crosslinker. The hydrolysable crosslinker may be present in the crosslinked copolymer hydrogel in an amount that ranges from 0.05% to 10% w/w crosslinker, such as 0.1% to 9% w/w, such as 0.5% to 8% w/w, such as 0.75% to 7% w/w and including 1% to 5% w/w. Depending on the protocol employed to crosslink the subject hydrogels, the crosslink density may vary. In certain instances, the hydrogel is crosslinked by chemical crosslinking. As such, the crosslink density may vary depending on the type and concentration of chemical crosslinking agent employed. Alternatively, the hydrogel may be photocrosslinked and the crosslink density may vary depending on the intensity of electromagnetic radiation contacted with the hydrogel composition as well as the duration of irradiation. In some embodiments of the invention, the crosslink density of the subject crosslinked copolymer hydrogels may range, such as from $1 \times 10^{-15}$ moles/cm$^3$ to $1 \times 10^{-3}$ moles/cm$^3$. Accordingly, depending on the amount of crosslinking, the swelling ratio of the subject hydrogels may vary, ranging such as from 1 to 35. Likewise, the compressive modulus of the hydrogels may vary, ranging such as from 1 kPa to 35 kPa. See, for example, co-pending international Patent Application PCT/US2014/033512, herein specifically incorporated by reference.

A hydrogel formulation optionally includes fibrinogen. The fibrinogen may be incorporated into the hydrogel composition before or after the hydrogel has been crosslinked. For example, in some instances fibrinogen is added to the hydrogel precursor composition. Fibrinogen may be present in the crosslinked copolymer hydrogel in an amount that ranges from 0.05% to 50% w/w fibrinogen, such as from 0.1% to 45% w/w, such as from 0.5% to 40% w/w, such as from 0.75% to 35% w/w, such as from 1% to 30%, such as from 2% to 20%, such as from 5% to 15% and including 10% w/w.

The hydrogels may be synthesized to achieve a certain release profile. In some embodiments, crosslinked copolymer hydrogels provided by the invention are configured to release HB-EGF or an HB-EGF agent under physiological conditions at a substantially zero-order release rate. In other embodiments, the subject crosslinked copolymer hydrogels are configured to release HB-EGF or an HB-EGF agent under physiological conditions at a substantially first-order release rate. In yet other embodiments, the subject crosslinked copolymer hydrogels are configured to release HB-EGF or an HB-EGF agent under physiological conditions at a substantially second-order release rate. In certain embodiments, the subject crosslinked copolymer hydrogels are configured to have a release profile that includes: 1) a first period where HB-EGF or an HB-EGF agent is released from the hydrogel at a first predetermined rate; and 2) a second period where HB-EGF or an HB-EGF agent are released from the hydrogel at a second predetermined rate.

In some embodiments of the invention, the ratio of chitosan to the polyester in the hydrogel may vary, in some embodiments ranging between 10:1 and 9.5:1; 9.5:1 and 9:1; 9:1 and 8.5:1; 8.5:1 and 8:1; 8:1 and 7.5:1; 7.5:1 and 7:1; 7:1 and 6.5:1; 6.5:1 and 6:1; 6:1 and 5.5:1; 5.5:1 and 5:1; 5:1 and 4.5:1; 4.5:1 and 4:1; 4:1 and 3.5:1; 3.5:1 and 3:1; 3:1 and 2.5:1; 2.5:1 and 2:1; 2:1 and 1.5:1; 1.5:1 and 1:1 or a range thereof. For example, the mass ratio of the chitosan component to the polyester component may range from 10:1 and 1:1, such as 8:1 and 1:1, such as 5:1 and 1:1, such as 4:1 and 1:1, and including from 2:1 and 1:1. In certain instances, the ratio of chitosan to the polyester is 1:1. In other embodiments, the ratio of chitosan to the polyester may vary, in some embodiments ranging between 1:1 and 1:1.5; 1:1.5 and 1:2; 1:2 and 1:2.5; 1:2.5 and 1:3; 1:3 and 1:3.5; 1:3.5 and 1:4; 1:4 and 1:4.5; 1:4.5 and 1:5; 1:5 and 1:5.5; 1:5.5 and 1:6; 1:6 and 1:6.5; 1:6.5 and 1:7; 1:7 and 1:7.5; 1:7.5 and 1:8; 1:8 and 1:8.5; 1:8.5 and 1:9; 1:9 and 1:9.5; 1:9.5 and 1:10 or a range thereof. For example, the ratio of chitosan to the polyester may range from 1:1 and 1:10, such as 1:1 and 1:8, such as 1:1 and 1:5, such as 1:1 and 1:4, and including from 1:1 and 1:2.

Crosslinked copolymer hydrogels may be 1 kDa or greater, such as 2 kDa or greater, such as 3 kDa or greater, such as 5 kDa or greater, such as 10 kDa or greater, such as 15 kDa or greater, such as 20 kDa or greater, such as 25 kDa or greater, such as 30 kDa or greater, such as 40 kDa or greater, such as 50 kDa or greater, such as 60 kDa or greater and including 75 kDa or greater.

After pharmaceutical compositions have been prepared, they can be placed in an appropriate container and labeled for treatment of an indicated condition. For administration of a composition of the invention, such labeling would include amount, frequency, and method of administration.

Combination Formulations

The formulations of the invention may comprise an effective dose of HB-EGF in combination with a second active agent, particularly other antimicrobial agents. For example, other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Antiviral agents, e.g. acyclovir, gancyclovir, etc., may be included.

Cytokines and growth factors also find use in combination with HB-EGF, e.g. growth factors, such as transforming growth factor (TGF)-β, platelet-derived growth factor (PDGF), fibroblast growth factor (FGF), and epidermal growth factor (EGF), VEGF, tumor necrosis factor-α (TNF-α), endothelin-1, keratinocyte growth factor, and the like. See, e.g., Steed, D. et al., *J. Am. Call. Surg.* 183:61-64 (1996); Richard, J. et al., *Diabetes Care* 18: 64-69 (1995); Steed, D. *J. Vasc. Surg.* 21:71-78 (1995); Kelley, S. et al., *Proc. Soc. Exp. Biol.* 194:320-326 (1990).

Methods of Use

According to the invention, wound healing of a chronic perforation of the tympanic membrane is improved by providing or enhancing the levels of HB-EGF. This may be accomplished in several different ways. For instance, a patient may be treated with an effective amount of an active agent such as, e.g., a drug, hormone, cytokine, anti-body, or another compound that up-regulates the expression of HB-EGF; reduces the degradation of HB-EGF; or increases the local or systemic levels of HB-EGF or a HB-EGF homolog or derivative. Nucleic acids encoding HB-EGF may also be administered for therapeutic purposes.

Typically a formulation comprising an HB-EGF protein, e.g. the soluble form of human HB-EGF, is topically administered to an individual suffering from a chronic TM perforation via the outer ear canal, for a period of time sufficient to substantially close the perforation. The human or non-human subject may or may not suffer from a condition which impairs or slows down the healing of the tympanic membrane perforation.

The invention provides HB-EGF or HB-EGF inhibitor compositions, which, when administered in an effective amount, results in an increased or decreased HB-EGF level in the wound area of a subject. For example, for acceleration of tympanic membrane healing, a composition comprising HB-EGF can be applied to the area surrounding a tympanic membrane perforation. HB-EGF inhibitor can also be applied to inhibit normal or excess wound healing. In the case of HB-EGF compositions, for acceleration of tympanic membrane healing, a composition can be applied to the area adjacent or local to a tympanic membrane perforation. They can be applied via any biodegradable or non-biodegradable source or structure.

In another embodiment, the method of invention is applied to inhibit the healing of a perforated tympanic membrane in a subject. The human or non-human subject may or may not suffer from a condition which impairs or slows down the healing of the tympanic membrane perforation. For example, such methods can be applied as a replacement for myringotomy and insertion of tympanostomy tubes, which is commonly prescribed for chronic otitis media, malformation of the ear drum or Eustachian tube, Down's syndrome, cleft palate, and barotrauma (middle ear injury caused by a reduction of air pressure), etc. Conventionally a tympanostomy tube is inserted into the TM, and maintained for an extended period of time, e.g. up to one month, up to 2 months, up to 3 months, up to 4 months, up to 6 months, or more.

The methods also find use in the generation of an animal model that provides a clinically relevant model for human perforated eardrum conditions. In such models, the animal may be any convenient laboratory animal, e.g. rodents, lagomorphs etc., and including without limitation mice, rats, guinea pigs, rabbits, cats, dog, non-human primates; and the like.

In such embodiments, an effective dose of an inhibitor of EGFR ligand shedding is administered, usually by topical contact to the tympanic membrane, to create a perforation of the TM. In some such embodiments, a small perforation may be initially made, e.g. an area of from about 0.1 to 10 $mm^2$, from about 0.1 to about 5 $mm^2$, from about 0.1 to 2.5 $mm^2$, from about 0.1 to about 1 $mm^2$. Following the initial perforation, the wound is contacted with an effective dose of an HB-EGF inhibitor, in a formulation and for a period of time as provided herein. An active dose of the inhibitor can be maintained for the length of time that the perforation is desired.

Kits

Another aspect of the invention provides a kit for treatment of chronic perforation of the TM. The kit includes a formulation that provides for an effective dose of HB-EGF, e.g. in the form of drops, devices, formulations, and the like. The kit may also include a delivery device, e.g. ear drop dispenser, syringe for delivery of a formulation, dual barrel syringe for delivering a two part formulation; and the like. The kit may also comprise instructions for use.

Alternatively a kit can be provided for generating a chronic perforation of the TM. The kit includes a formulation that provides for an effective dose of an HB-EGF inhibitor, e.g. in the form of drops, devices, formulations, and the like. The kit may also include a delivery device, e.g. ear drop dispenser, syringe for delivery of a formulation, dual barrel syringe for delivering a two part formulation; and the like. The kit may also comprise instructions for use. The kit may further comprise a sterile needle or lancet for generating an initial perforation in the TM.

Example 1

Inhibition of HB-EGF

HB-EGF is critical to epidermal wound healing in a tympanic membrane model. The normalized signal intensity of HB-EGF like growth factor following perforation of the tympanic membrane in rats shows an 8.5 fold up regulation of HB-EGF like growth factor. Experimental inhibition of HB-EGF activity is shown herein to prevent a tympanic membrane perforation from healing.

Figure 5:
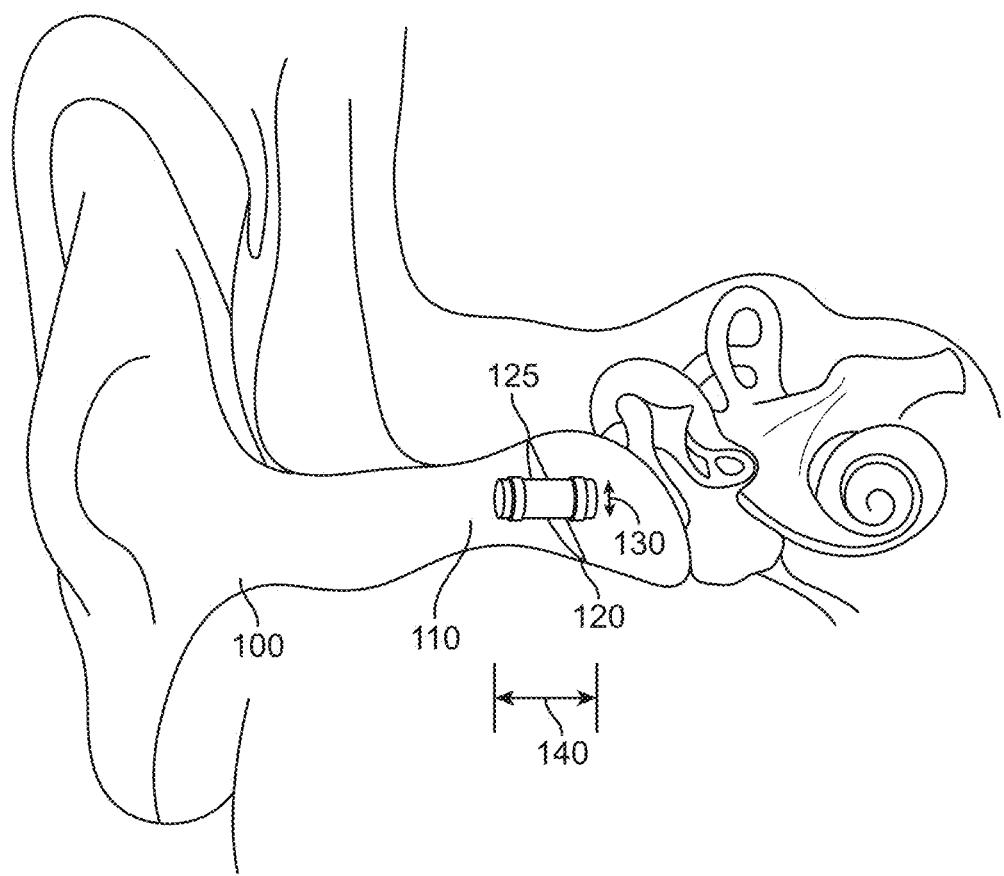
FIG. 5 depicts the ear canal 100; external ear 110; and tympanic membrane 120. A transmembrane drug delivery device 125 is also depicted, which has a width 130 and length 140.

EGFR ligand shedding can be inhibited to create a chronic tympanic membrane perforation model. Subtotal perforations were created in the pars tensa of TMs in 20 mice using a curved needle. OSU8.1 (10 mM), a selective HB-EGF inhibitor (see Tokumaru et al. (2000) J. Cell Biol.), was injected onto gel foam (placed through and onto the perforation) over seven days. Mice were sacrificed at time points (Day 2, 7, 14, 30, 44, 60 and 90) to observe the effects on keratinocyte migration. The contralateral ear was used as a control with saline placed onto gel foam. All of these were closed within 2 weeks. Five of seven (71%) of the treatment ears were open at three months. Representative images of chronic TM perforation are shown in FIG. 5. Perforation size was stable over three months (using ImageJ to calculate the perforation area as a percentage of the pars tensa area). A larger cohort was undertaken with 87.9% (n=58) having chronic perforations at 3 months. Our preliminary study has for the first time suggested an established, reproducible growth factor based chronic TM animal model.

Table 1 shows the results of applying HB-EGF inhibitor (OSU8-1) to acute tympanic perforations in mice. 100% of HB-EGF inhibitor treated perforations were present at two months compared to 5% of controls and 71% were present at three months compared to 5% of controls

TABLE 1

| Cohort | Perforations open at 2 months | Perforations open at 3 months |
| --- | --- | --- |
| Control | 5% (n = 21) | 5% (n = 19) |
| HB-EGF inhibitor | 100% (n = 9) | 71% (n = 7) |

Creating an Animal Model for Chronic Suppurative Otitis Media.

After creating the chronic perforation model with ET occlusion, two types of bacteria were inoculated into the middle ear through the existing chronic perforations. At 2 weeks the ear fluid was collected and sent for polymerase chain reaction (PCR) to test for the presence of bacteria. The bacteria chosen were two of the most common involved in chronic ear disease, *streptococcus pneumonia* type 3 (dose of $6\times10^6$ colony forming units per ml) and *pseudomonas aeruginosa* (dose of $6\times10^9$ colony forming units per ml).

Example 2

Treatment of Chronic Tympanic Membrane Perforation

The efficacy of HB-EGF treatment for chronic TM perforations is demonstrated.

A Biocompatible Absorbable Injectable Polymer for Growth Factor Delivery in Ear Canal.

To treat chronic TM perforation, it is desirable to have a liquid that can be dropped into the ear, which then hardens and slowly resorbs over the designated time frame while eluting out the medication. The degradation rate of the polymer and drug eluting rate are readily adjustable according to target of interest.

A biodegradable chitosan-based hydrogel for delivering growth factors was developed to provide a biocompatible, bioresorbable, injectable polymer that can carry a drug of choice and then can be instilled into the ear canal. The gel has two liquid components and can solidify within a few minutes after mixing the two components. This can be readily administered by a dual-bore syringe. Alternatively the solutions can be mixed with a crosslinking agent prior to delivery, and instilled with a single bore syringe.

The newly-developed chitosan-based hydrogel comprises of hydrophilic chitosan backbone molecules and hydrophobic polylactide side chains. Fibrinogen can be incorporated into the co-polymer networks to improve binding affinity, enhance cell attachment, and provide proteolytically degradable sites. Drug release from the polymeric hydrogel varies according to the characteristics such as hydrophilic affinity, swelling behavior, degradability, and crosslinking density of the polymer. The drug release profiles of rhBMP-2 from chitosan-based hydrogels was measured, and the degradation behavior of the polymeric hydrogel in a variety of conditions.

The specific ratio of chitosan to polylactide for the gel used in the present examples is 8:1. In addition, 10% w/w of fibrinogen is incorporated into the prepolymer solution. The hydrogel formulation can solidify within a few minutes after mixing with a catalyst for chemical crosslinking. This can be readily administered by a dual-bore syringe, or with a single bore syringe.

Hydrogels are Non-Ototoxic.

Figure 2:
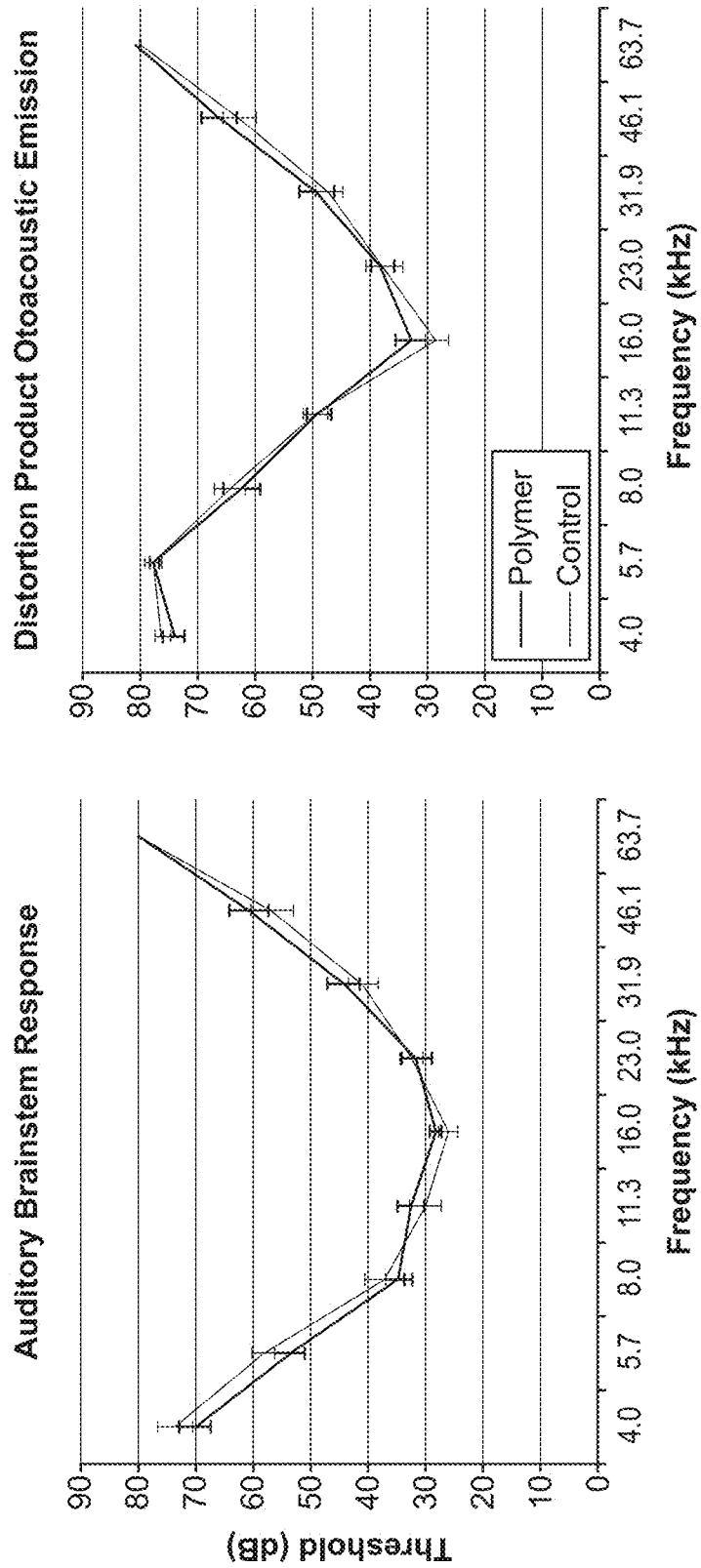
FIG. 2. ABR and DPOAE thresholds were measured 60 days after both eardrums were surgically perforated in 9 mice. One ear had no injection (control), whereas the opposite ear was filled with polymer delivery vehicle of chitosan, fibrinogen and polylactide.

The hydrogels were injected into mice eardrums following perforations. One ear was filled with the polymer, whereas the opposite ear had no injection (control). Auditory brainstem response (ABR) and distortion product otoacoustic emission (DPOAE) thresholds were measured 60 days after both eardrums were surgically perforated in 9 mice. By the time that the eardrums healed spontaneously, there were no differences in auditory thresholds between the two sides (FIG. 2). The data show that the hydrogels are non-ototoxic.

HB-EGF Heals Chronic Tympanic Membrane Perforations.

When a cohort of chronic perforations in mice ears were treated with 40 µl of a gel containing recombinant HB-EGF at a concentration of 5 µg/ml (sustained release dose via a bioabsorbable chitosan-based polymer) 92% (22 of 24) healed, compared to 38% (10 of 26) of controls (polymer only) at 4 weeks ($p<0.01$). The ability to overcome this critical step in TM chronic wound healing using GF to activate GFR ectodomain ligand shedding demonstrates its suitability for intervention using a biotherapeutic. This is the first growth factor treatment tested in an animal model of chronic perforation that has shown significant benefit over control.

HB-EGF Heals Chronic Tympanic Membrane Perforations with Eustachian Tube Occlusion.

An animal model of chronic TM perforation and ET occlusion was created, as shown in FIG. 3. An existing rat model of ET occlusion (see Herda et al. (2002) Laryngoscope 112:1657-62) was adapted to the mouse and has since been performed in 80 live mice with success. The ET occlusion was performed with the chronic perforation model described above. This created a wet sterile discharging perforation at 3 months. This model mimics the human condition of chronic perforation combined with ET dysfunction.

Figures 4A, 4B:
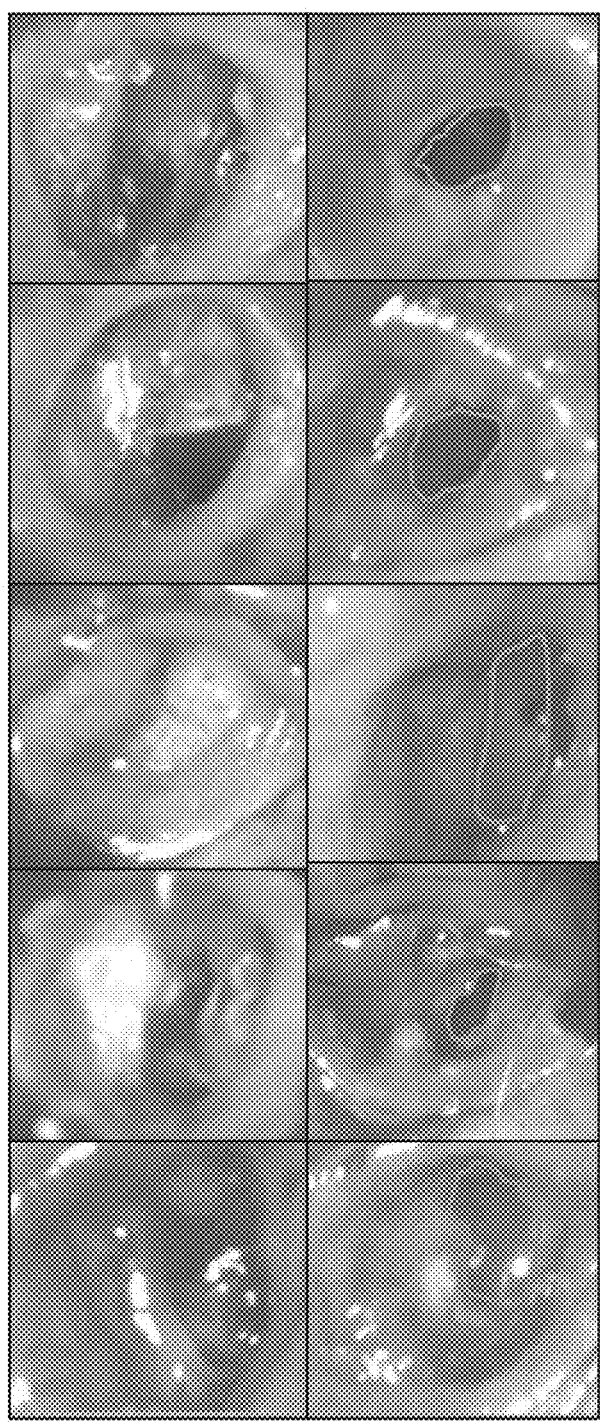
FIG. 4A-4B. GF treatment of chronic perforations in a mice model of ET occlusion. The top row (FIG. 4A) are representative images of the treatment group showing healed perforations. The bottom row (FIG. 4B) are representative images of the control (polymer only) group showing persisting perforation (outline blue). Note: some TMs in the top role have healed with tympanosclerosis.

When a cohort of mice with this model (chronic perforations and ET occlusion) were treated with recombinant HB-EGF, 40 µl at a concentration of 5 µg/ml (sustained release dose via a bioabsorbable chitosan polymer) 94% (18 of 19) healed compared to 9% (2 of 23) of controls (polymer only) at 6 weeks ($p<0.01$). Representative images of healed or non-healing chronic TM perforations are shown in FIG. 4. Histologically the perforations close with thick layer of keratinocytes, compared to controls with a lack of keratinocyte layer even in those few cases that closure occurred. The ability to overcome this critical step in TM chronic wound healing using HB-EGF to activate EGFR ectodomain ligand shedding in the presence of middle ear effusions and ET occlusion is useful in treating patients with chronic tympanic membrane perforation.

Testing in an Animal Model for Chronic Suppurative Otitis Media.

After creating the chronic perforation model with ET occlusion, *Pseudomonas aeruginosa* (dose of $6\times10^9$ colony forming units per ml) were inoculated into the middle ear through the existing chronic perforations. At 2 weeks the ear fluid was collected and sent for polymerase chain reaction (PCR) to confirm the presence of bacteria. This positive PCR validated the CSOM model.

The mice were then divided into two cohorts. One received polymer only. The other received polymer and HB-EGF at 5 µg/ml (same dose used in above models). 100% of the HB-EGF group healed (16 of 16) compared to 41% (7/17) in the control group ($p<0.01$). In the control group the healing was also different when it did occur. The TM was often very thin and transluscent compared to a slightly opaque normal TM. The healing in the HB-EGF group appeared normal. The ability to still overcome this critical step in TM chronic wound healing using HB-EGF to activate EGFR ectodomain ligand in the closest model to human CSOM validates the method of treatment.

Example 3

Figure 6:
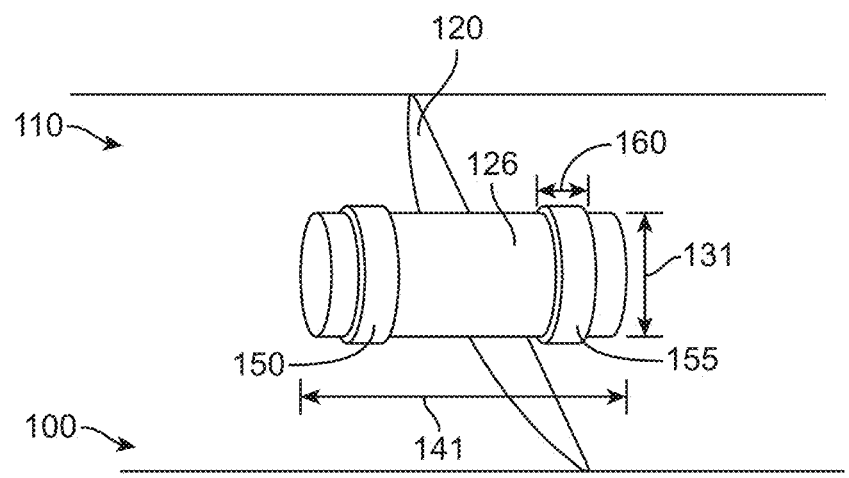
FIG. 6 depicts an alternative embodiment of a trans-tympanic delivery device 126. The device has a width 131 and length 141. The device 126 comprises one or both of an external restraint 150 and internal restraint 155, where the restraint has a width 160.

A trans-tympanic method of delivery (FIGS. 5, 6 and 7). The vehicle for HB-EGF or HB-EGF delivery is placed against or through the tympanic membrane inserted either trans-canal or via the Eustachian tube. It can be removed after a period of time, or can be biodegradable. The vehicle may contain a design to restrain it within the tympanic membrane. This may be a collar, cuff, flange, groove or any change in width or height. It may have more than one of these to hold it in place. The vehicle may be perforated or have a lumen of any suitable dimension. There may be any number of flanges or any width and dimensions that are deemed sufficient or in excess of that required for the vehicle to be retained in the tympanic membrane.

Depicted in FIG. 5 is the ear canal 100; external ear 110; and tympanic membrane 120. A transmembrane drug delivery device 125 is also depicted, which has a width 130 and length 140.

Depicted in FIG. 6 is an alternative embodiment of a trans-tympanic delivery device 126. The device has a width 131 and length 141. The device 126 comprises one or both of an external restraint 150 and internal restraint 155, where the restraint has a width 160.

Figure 7A:
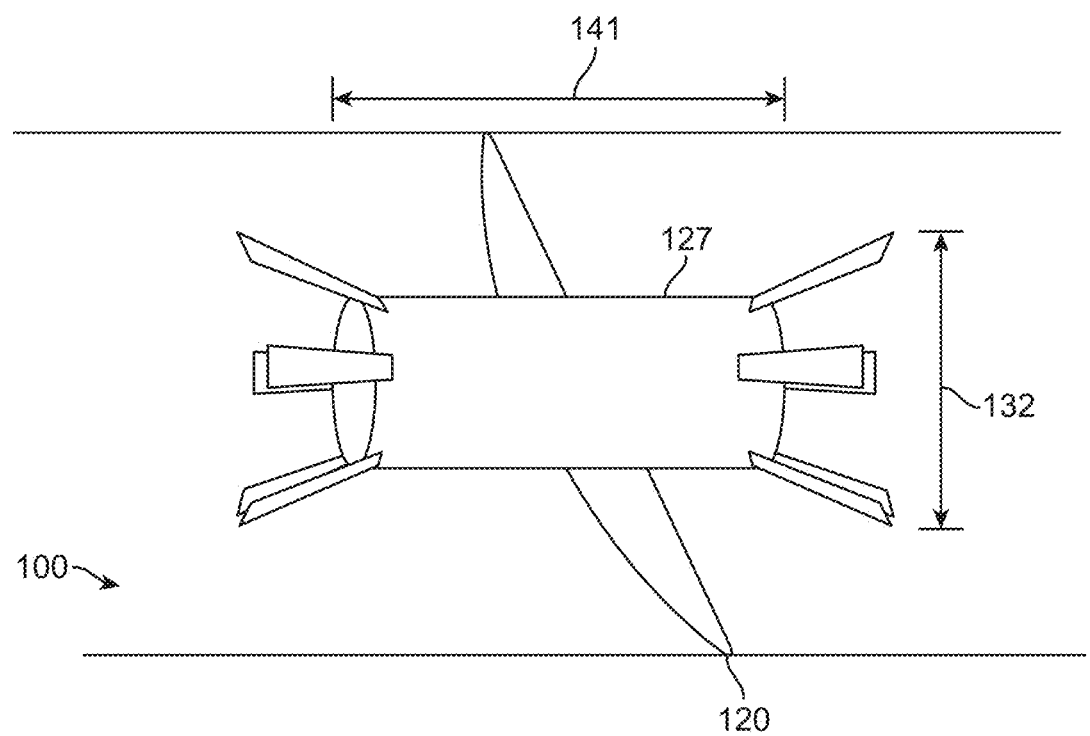
FIG. 7A-7B depict another embodiment of a trans-tympanic delivery device 127.
Figure 7B:
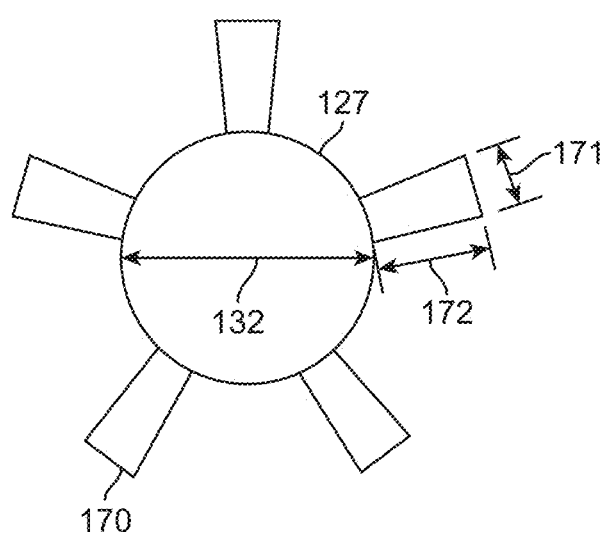

Depicted in FIGS. 7A-7B is another embodiment of a trans-tympanic delivery device 127. FIG. 7A is a top view showing the ear canal 100 and tympanic membrane 120. The delivery device 127 has a width 132 and length 142. The device comprises a plurality of flanges, 170, arranged lengthwise along the device, which flanges have a length 171 and width 172. FIG. 7B depicts a cross-section of the device.

Example 4

Intra-Tympanic Delivery Device

The growth factor delivery device can be placed between the layers of the tympanic membrane. If a solid vehicle, it can be placed by lifting one or more layers as a flap then replacing the flap after placement. If liquid it can be injected.

Figure 8:
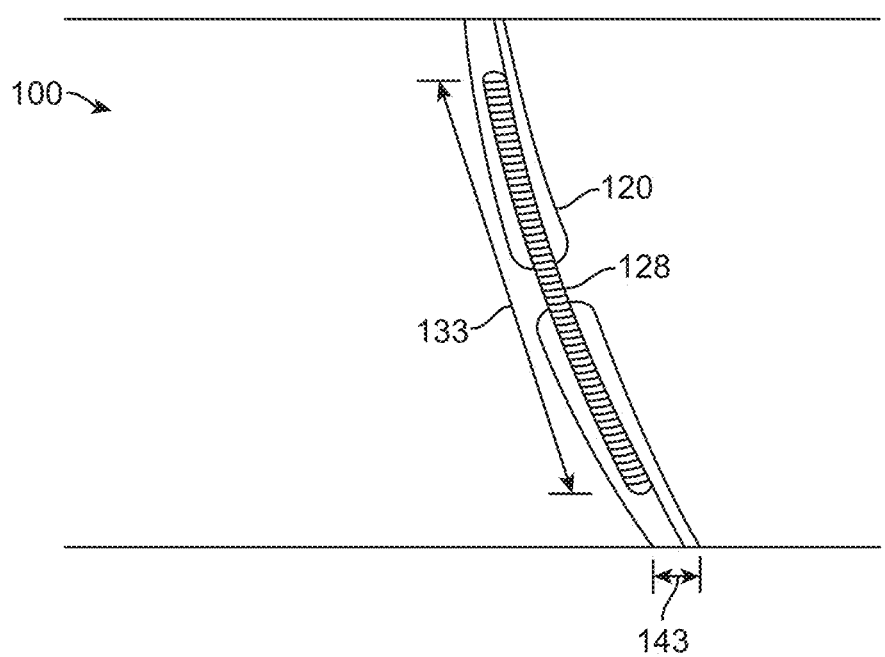
FIG. 8 depicts an intra-tympanic membrane delivery device 128. The device is inserted in the tympanic membrane, 120. The device has a width 133 and length 143.

Depicted in FIG. 8 is an intra-tympanic membrane delivery device 128. The device is inserted in the tympanic membrane, 120. The device has a width 133 and length 143.

Example 5

Figure 9:
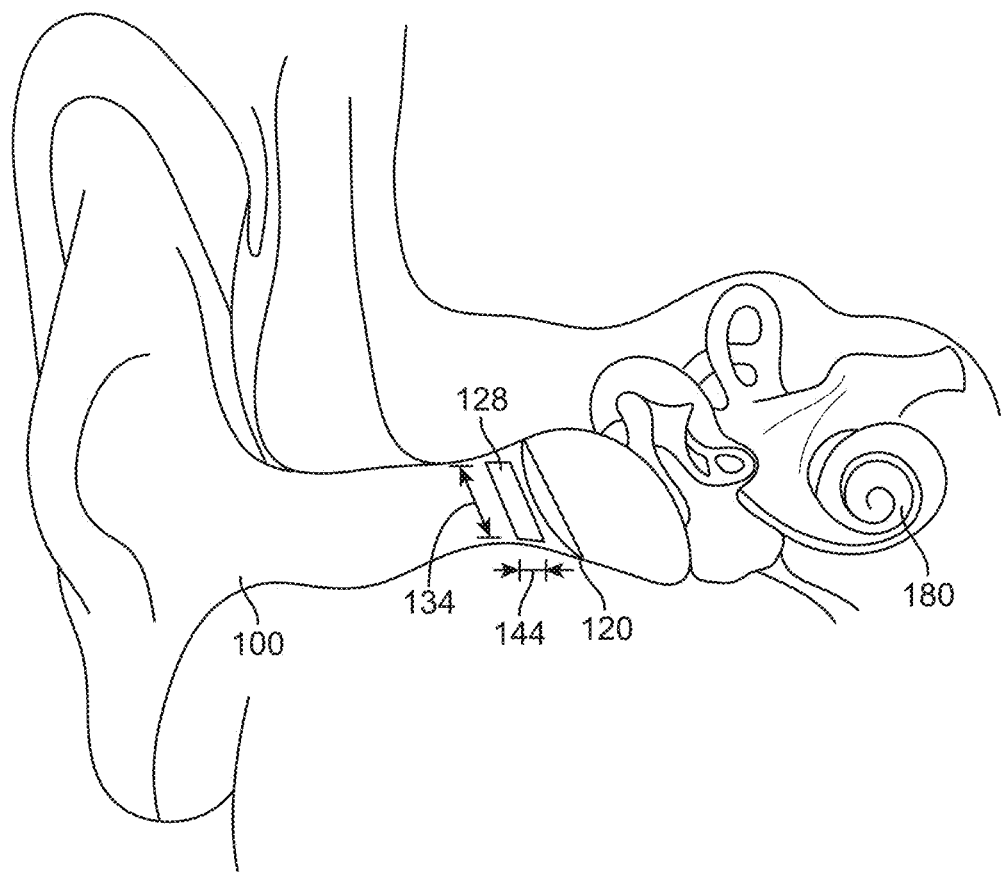
FIG. 9 depicts a growth factor delivery device 128 adjacent to the tympanic membrane 120. The device has a width 134 and length 144.

Placement of vehicle as a solid object adjacent to the tympanic membrane (FIG. 9). The vehicle may be placed against the tympanic membrane and provide a local source of HB-EGF or HB-EGF inhibitor. The vehicle may be placed medial or lateral with part or all through the tympanic membrane. The part through the tympanic membrane may be smaller, larger or the same size as the perforation if present.

Depicted in FIG. 9 is a growth factor delivery device 128 adjacent to the tympanic membrane 120. The device has a width 134 and length 144.

Example 6

Figure 10:
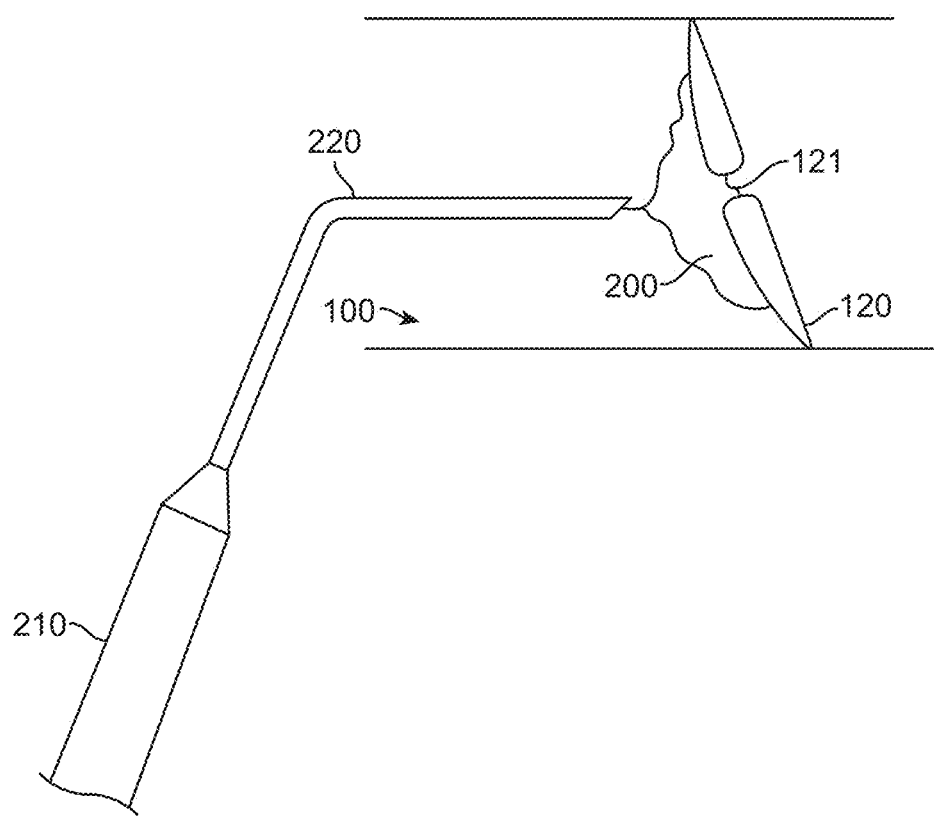
FIG. 10 depicts an injectable method of growth factor application. The formulation comprising growth factor 200 can be delivered into the ear canal 100 to make contact with the tympanic membrane 120 on its lateral and/or medial surface, and may further flow into the region of a tympanic membrane perforation 121. The formulation can be dispensed from a syringe 210, through a delivery tube 220. The formulation can be provided as a single solution, or as two solutions that are mixed at the time of delivery.

An injectable method of growth factor application is shown in FIG. 10. The formulation comprising growth factor 200 can be delivered into the ear canal 100 to make contact with the tympanic membrane 120 on its lateral and/or medial surface, and may further flow into the region of a tympanic membrane perforation 121. The formulation can be dispensed from a syringe 210, through a delivery tube 220. The formulation can be provided as a single solution, or as two solutions that are mixed at the time of delivery.

Dual chamber syringes are known in the art and readily available, e.g. see among others: Lyo-Ject® dual-chamber syringe; or any one of U.S. Pat. No. 5,971,953; U.S. Patent applications US20030040701; US20140012196; US 20130060232; International application WO1999017820A1; etc.

Such formulations include compositions that, upon mixture, change to a more viscous or solid state. Viscogenic agents include, without limitation, gellan, N-isopropyl acrylamide with sodium acrylate and n-N-alkylacrylamide, polyacrylic acid with polyethylene glycol, polymethacrylic acid with polyethylene glycol, CARBOPOL® with hydroxypropylmethylcellulose, cellulose acetate hydrogen phthalate latex, sodium alginate, or a reverse thermosetting gel such as a poloxamer or a poloxamine.

Such formulations can be delivered to the external, epidermal surface of the tympanic membrane in a liquid-like state, i.e., a flowable form. After administration, however, the composition transforms into a solid-like state such that the composition remains in contact with the tympanic membrane. As a result, the composition remains localized against the tympanic membrane and the pharmacologic agent can transfer to the tympanic membrane. The viscous or solid composition may be biodegradable or non-biodegradable.

What is claimed is:

1. A method to promote closing of a chronic tympanic membrane perforation that has not healed after at least 2 months in an individual human, the method comprising:
    contacting a site of the chronic tympanic membrane perforation with a liquid formulation comprising an effective dose of a human heparin binding epidermal growth factor (HB-EGF) protein, wherein the liquid formulation is mixed with a viscogenic agent or cross-linking agent before or concurrently with said contacting the site of the chronic tympanic membrane perforation with the liquid formulation, wherein the liquid formulation transforms into a more viscous state or a gel that remains localized against the tympanic membrane and provides for sustained release of the HB-EGF for a period of time that is 7 days or longer,
    to promote closing of the chronic tympanic membrane perforation.

2. The method of claim 1, wherein the liquid formulation comprises polymer components, wherein said mixing with the cross-linking agent is performed before or concurrently with said contacting the site of the chronic tympanic membrane perforation with the liquid formulation to transform the liquid formulation into a sustained release cross-linked copolymer hydrogel.

3. The method of claim 1, wherein the liquid formulation further comprises at least one additional active agent.

4. The method of claim 1, wherein the HB-EGF is present in solution in the liquid formulation.

5. The method of claim 1, wherein the gel is a reverse thermosetting gel.

6. The method of claim 1, wherein the HB-EGF is a soluble mature form of HB-EGF.

7. The method of claim 1, wherein the method results in closure of the chronic tympanic membrane perforation.

8. A method to promote closing of a chronic tympanic membrane perforation that has not healed after at least 2 months in an ear of an individual human, the method comprising:
    contacting a site of the chronic tympanic membrane perforation with a liquid formulation comprising at least 1 mg/ml and up to 500 mg/ml of a soluble mature form of human heparin binding epidermal growth factor (HB-EGF) protein, wherein the liquid formulation is mixed with a viscogenic agent or cross-linking agent before or concurrently with said contacting the site of the chronic tympanic membrane perforation with the liquid formulation, wherein the liquid formulation transforms into a more viscous state or a gel that remains localized against the tympanic membrane and provides sustained release of the HB-EGF for a period of time 7 days or longer,
    to promote closing of the chronic tympanic membrane perforation.

9. The method of claim 8, wherein up to 500 µl of the liquid formulation is delivered to the ear.

10. The method of claim 9, wherein the method results in closure of the chronic tympanic membrane perforation.

11. A method to promote closing of a chronic tympanic membrane perforation that has not healed after at least 2 months in an ear of an individual human, the method comprising:
    contacting a site of the chronic tympanic membrane perforation with a liquid formulation comprising at least 1 mg/ml and up to 500 mg/ml of a soluble mature form of human heparin binding epidermal growth factor (HB-EGF) protein, wherein the liquid formulation is mixed with a viscogenic agent or cross-linking agent before or concurrently with said contacting the site of the chronic tympanic membrane perforation with the liquid formulation, wherein the liquid formulation transforms into a more viscous state or a gel that remains localized against the tympanic membrane and provides sustained release of the HB-EGF for a period of time that is 3 days or longer,
    to promote closing of the chronic tympanic membrane perforation.

12. The method of claim 11, wherein up to 500 µl of the liquid formulation is delivered to the ear.

13. The method of claim 12, wherein the method results in closure of the chronic tympanic membrane perforation.

14. A method to promote closure of a chronic tympanic membrane perforation in a human subject, the method comprising: mixing a liquid formulation comprising chitosan, polylactic acid, fibrinogen, and an effective dose of human heparin binding epidermal growth factor (HB-EGF) protein with a cross-linking agent immediately before administering the formulation to the site of said perforation, wherein the mixture forms a sustained release cross-linked copolymer hydrogel against the tympanic membrane and wherein the chronic tympanic membrane perforation in the human subject completely closes.

15. The method of claim 14, wherein a single or dual-bore syringe is used for administration.

16. The method of claim 14, wherein the ratio of chitosan to polylactide is 8:1.

17. The method of claim 14, wherein the liquid formulation contains 10% w/w fibrinogen.

18. The method of claim 14, wherein the hydrogel is in contact with the tympanic membrane for a period of at least 7 days.

* * * * *